(12) United States Patent
Sanada

(10) Patent No.: US 8,323,699 B2
(45) Date of Patent: Dec. 4, 2012

(54) METHOD OF MANUFACTURING SKIN CARE CREAM CONTAINING BAKED SHELL POWDER

(75) Inventor: Kazunobu Sanada, Tokyo (JP)

(73) Assignee: Kabushiki Kaisha Asadasyokai, Tokyo (JP)

( * ) Notice: Subject to any disclaimer, the term of this patent is extended or adjusted under 35 U.S.C. 154(b) by 188 days.

(21) Appl. No.: 12/656,077

(22) Filed: Jan. 15, 2010

(65) Prior Publication Data

US 2010/0173017 A1  Jul. 8, 2010

Related U.S. Application Data

(62) Division of application No. 11/884,023, filed on Aug. 9, 2007, now abandoned.

(30) Foreign Application Priority Data

Feb. 10, 2005 (JP) .................................. 2005-066248
Sep. 5, 2005 (JP) .................................. 2005-291659

(51) Int. Cl.
*A61K 35/56* (2006.01)
*A61K 33/08* (2006.01)
*A61K 33/10* (2006.01)
*A01N 59/06* (2006.01)

(52) U.S. Cl. ......................... 424/547; 424/693; 424/687

(58) Field of Classification Search ....................... None
See application file for complete search history.

(56) References Cited

U.S. PATENT DOCUMENTS 5,084,279 A * 1/1992 Kato et al. ..................... 424/547
2004/0028748 A1 * 2/2004 Sasaya ......................... 424/547

FOREIGN PATENT DOCUMENTS

JP 2001048748 A * 2/2001

* cited by examiner

*Primary Examiner* — James H. Alstrum-Acevedo
*Assistant Examiner* — Jessica Kassa
(74) *Attorney, Agent, or Firm* — Manabu Kanesaka

(57) ABSTRACT

In a method of manufacturing a skin care cream containing baked shell powder, highly calcium-containing shells such as dead shells or pearls is baked and crushed to fine powder to obtain baked shell powder. Then, the obtained baked shell powder is added to mix with a raw material for manufacturing cosmetic cream.

9 Claims, 3 Drawing Sheets

Fig. 1(a)

| age | sex | purpose of use | effect | specific effect | period of use | Irritation | itch | side effect |
|---|---|---|---|---|---|---|---|---|
| 57 | male | cure for athlete's foot | yes | Itch disappeared and was cured | 1 day | no | no | no |
| 38 | male | cure for athlete's foot | yes | Itch disappeared | 1 month | no | no | no |
| 35 | male | cure for athlete's foot | yes | Itch stopped | 10 days | no | no | no |
| 57 | male | cure for athlete's foot (feet) | yes | Felt like to have "a smooth skin" | 7 days | no | no | no |
| 50 | male | cure for athlete's foot | yes | Itch disappeared | 3 days | no | no | no |
| 59 | male | cure for athlete's foot | yes | Itch stopped and the skin peeled off to cure the athlete's foot | 4 days | no | no | no |
| 66 | male | cure for athlete's foot | yes | The skin peeled off to become dry and cure the athlete's foot | 4 days | no | no | no |
| 28 | male | cure for athlete's foot | yes | Itch stopped | 2 days | no | no | no |
| 44 | female | atopy | yes | Itch disappeared and the skin became whiter | 10 days | no | no | no |
| 18 | female | atopy | yes | Itch disappeared | 3 days | no | no | no |
| 29 | female | atopy | yes | Itch disappeared and the skin became whiter | 10 days | no | no | no |
| 15 | male | atopic dermatitis | yes | Itch due to atopy stopped and the skin peeled off and became clean | 1 month | no | no | no |
| 49 | male | became unable to speak out due to cold | yes | The subject became able to speak out after 5 minutes and a gargling | 1 day | no | no | no |
| 67 | male | chapped skin | yes | | 1 month | no | no | no |
| 46 | female | as anti-spot measure and to make skin whiter | yes | The spots became less remarkable and friends told that the face had become whiter | 2 months | no | no | no |

Fig. 1(b)

| | | | | | | | | |
|---|---|---|---|---|---|---|---|---|
| 30 | female | as anti-spot measure and to make skin whiter | yes | The spots became less remarkable | 10 days | no | no | no |
| 45 | female | as anti-spot measure and to make skin whiter | yes | The spots became less remarkable | 14 days | no | no | no |
| 72 | female | as anti-spot measure (using cream) | yes | It seems to be ineffective to senile spots | | no | no | no |
| 36 | female | as anti-spot measure and to make skin whiter | yes | | 3 months | no | no | no |
| 52 | female | as anti-spot measure and to make skin whiter | yes | The cream provided an immediate effect | 2 months | no | no | no |
| 58 | female | as anti-spot measure and to moisture dry skin | yes | The cream was applied before sleeping at night and the skin was moisturized in the next morning | 5 days | no | no | no |
| 55 | female | as anti-spot measure and anti-freckle measure | no | | 7 days | no | no | no |
| 52 | female | as anti-spot measure and anti-freckle measure and to make skin whiter | | I am currently using the cream and cannot tell the effects yet | | no | no | no |
| 60 | female | as anti-spot measure | yes | The spots became less remarkable | 2 months | no | no | no |
| 29 | female | as anti-spot measure | yes | It seems that the spots became less remarkable | 3 days | no | no | no |
| 48 | female | as anti-spot measure | yes | The spots on the hands became less remarkable | 2 days | no | no | no |
| 63 | female | as anti-spot measure | yes | The spots on the hands became less remarkable and the skin became whiter. | 1.5 months | no | no | no |
| 59 | female | as anti-spot measure | yes | The spots became less remarkable after applying a month | 1 month | no | no | no |

Fig. 1(c)

| | | | | | | | |
|---|---|---|---|---|---|---|---|
| 55 | female | to make skin whiter | yes | It was effective to a small extent. There may be greater effects in more than 2 weeks | 7 days | no | no | no |
| 54 | female | to cure the keratinized elbow | yes | | 3 days | no | no | no |
| 65 | female | to remove the keratinized heel | yes | The keratin layer became softer. | 1 month | no | no | no |
| 30 | female | as anti-freckle measure | yes | It seems that the spots became less remarkable | 3 months | no | no | no |
| 42 | female | to cure the dry skin | yes | The feeling of dry skin disappeared | 7 days | no | no | no |
| 60 | female | as anti-dry-skin measure | yes | White scaly skin debris disappeared and the skin became moisturized | 5 days | no | no | no |
| 52 | female | to keep skin moisturized | yes | The cream was applied to the dry chin and hands. The foundation can be applied smoothly and the rough hand skin became smoother. | 14 days | no | no | no |
| 25 | male | to cure pimples | yes | The pimples disappeared | 10 days | no | no | no |
| 53 | male | to cure insect-bitten skin | yes | The itch stopped | 1 day | no | no | no |
| 32 | female | as anti-itch measure | yes | The cream became effective immediately | 1 day | no | no | no |
| 30 | male | to cure insect-bitten skin | yes | The cream became effective immediately | 1 day | no | no | no |
| 3 | female | to cure miliaria | yes | The itch and the red skin disappeared | 4 days | no | no | no |
| 5 | female | to cure miliaria | yes | The itch and the red skin disappeared | 7 days | no | no | no |
| 65 | male | to remove the scar of a burn | yes | Spots disappeared and the keloid became less remarkable | 1 month | no | no | no |

METHOD OF MANUFACTURING SKIN CARE CREAM CONTAINING BAKED SHELL POWDER

CROSS-REFERENCE TO RELATED APPLICATION

This is a divisional application of Ser. No. 11/884,023 filed on Aug. 9, 2007 now abandoned.

TECHNICAL FIELD

The present invention relates to a method of manufacturing a skin care cream containing baked shell powder that can suppress or cure inflammations of skin such as athlete's foot, miliaria and freckles and spots and exert anti-bacterial effects.

BACKGROUND ART

Known skin care creams that can suppress inflammations of skin such as athlete's foot and prickly heat include those produced by mixing mushrooms such as shiitake mushroom with silicon chloride, titanium chloride or zirconium chloride to dissolve them into the chloride and form a solution or by decomposing them with a strong acid to form a solution, adding water, alcohol or glycol to dilute the solution, then adding shell powder to the solution, immersing it in the solution, subsequently drying the shell powder and mixing it with greasy cream. Such skin care creams can cure hay fever, atopic dermatitis and athlete's foot by applying it to the affected part (see, inter alia, Patent Document 1).
Patent Document 1: JP 2004-26785-A

DISCLOSURE OF THE INVENTION

Problem to be Solved by the Invention

However, the above cited patent document disclosing the known skin care cream only describes the type of shell powder to be used for the product and does not describe any method of manufacturing such shell powder. The inventor of the present invention found that the therapeutic effects of a skin care cream that contains shell powder as an ingredient of a mixture is very weak and its effective period is short when shells are simply crushed for use.

Thus, it is the object of the present invention to provide a method of manufacturing a skin care cream that contains baked shell powder so as to make it able to exert strengthened anti-bacterial effects and effects of curing athlete's foot, miliaria and other skin diseases for a prolonged period of time.

Means for Solving the Problem

A skin care cream containing baked shell powder according to the present invention is manufactured by baking dead shells or pearls, crushing them to fine powder and adding the obtained baked shell powder to and mixing it with a raw material for manufacturing cosmetic cream.

More specifically, according to the present invention, there is provided a skin care cream containing baked shell powder and a method of manufacturing the same as defined below.

(1) A skin care cream containing baked shell powder is made by adding baked powder of highly calcium-containing shells such as dead shells or pearls to and mixing them with a raw material for manufacturing cosmetic cream.

(2) A skin care cream containing baked shell powder is made by adding baked powder of highly calcium-containing shells such as dead shells or pearls to the supernatant water obtained by mixing such baked shell powder with water, agitating the mixture and leaving the mixture still and then further adding the addition mixture to and mixing it with a raw material for manufacturing cosmetic cream.

(3) In the skin care cream containing baked shell powder according to (1) or (2) above, the baked shell powder is baked dead shell powder formed by baking/powdering or baked pearl powder formed by baking/powdering.

(4) In the skin care cream containing baked shell powder according to any one of (1) through (3) above, the temperature for baking shells is between 1,000 and 1,300° C.

(5) In the skin care cream containing baked shell powder according to any one of (1) through (4) above, unbaked shell powder is further added to and mixed with the raw material for manufacturing cosmetic cream.

(6) In the skin care cream containing baked shell powder according to (5) above, the baked shell powder is baked pearl powder and the unbaked shell powder is unbaked pearl powder.

(7) A method of manufacturing a skin care cream containing baked shell powder characterized by comprising:
a step of baking highly calcium-containing shells such as dead shells or pearls, crushing them to fine powder to obtain baked shell powder; and
a step of adding the obtained baked shell powder to and mixing it with a raw material for manufacturing cosmetic cream.

(8) A method of manufacturing a skin care cream containing baked shell powder comprises:
a first step of baking highly calcium-containing shells such as dead shells or pearls, crushing them to fine powder to obtain baked shell powder;
a second step of mixing the obtained baked powder with water, agitating the mixture, leaving the mixture still to obtain supernatant water;
a third step of adding the supernatant water obtained in the second step to the baked shell powder obtained in the first step and kneading the addition mixture; and
a fourth step of further adding the dough obtained in the third step to and mixing it with a raw material for manufacturing cosmetic cream.

(9) In the method of manufacturing a skin care cream containing baked shell powder according to (7) or (8) above, the baked shell powder is baked dead shell powder formed by baking/powdering or baked pearl powder formed by baking/powdering.

(10) In the method of manufacturing a skin care cream containing baked shell powder according to any one of (7) through (9) above, the temperature for baking shells is between 1,000 and 1,300° C.

(11) In the method of manufacturing a skin care cream containing baked shell powder according to any one of (7) through (10) above, unbaked shell powder is further added to and mixed with the raw material for manufacturing cosmetic cream.

(12) In the method of manufacturing a skin care cream containing baked shell powder according to (11) above, the baked shell powder is baked pearl powder and the unbaked shell powder is unbaked pearl powder.

Advantages of the Invention

A skin care cream containing baked shell powder according to the present invention can exert strengthened anti-bacterial effects and effects of curing athlete's foot, miliaria, freckles and other skin diseases for a prolonged period of time due to the baked shell powder.

Particularly, the powder particles of quicklime contained in the baked shell powder are coated with a greasy ingredient of the skin care cream so that the quicklime is not reduced to calcium carbonate by carbon dioxide in the air so that the skin care cream is not deteriorated with time. Therefore, the strong germicidal effect of quicklime is maintained for a long period of time.

Additionally, as a skin care cream is applied to the skin surface of human body, both the greasy ingredient and quicklime contact the skin surface microscopically so that only quicklime will not contact the skin surface to irritate the skin.

BRIEF DESCRIPTION OF THE DRAWING

FIG. 1 schematically illustrate some of the data obtained on the effects of the skin care cream containing baked shell powder of Examples.

BEST MODE FOR CARRYING OUT THE INVENTION

Now, the present invention will be described by way of an embodiment along with examples.

Highly calcium-containing shells that can be used for the purpose of the present invention include dead shells and spherical objects such as pearls that grow in shells. Dead shells that can be used for the purpose of the present invention include those of pearl oysters, goldlips, black lips scallops, abalones, oysters and clams.

To manufacture baked shell powder from shells, firstly dead shells or highly calcium-containing shells such as pearls are baked.

In a pre-processing step relative to the baking step, shells are roughly crushed, dried and then put into a baking furnace, where they are baked at 90 to 1,400° C., preferably at 1,000 to 1,300° C. for 60 minutes to 2 hours.

If shells are baked at temperature lower than 1,000° C., at 700° C. for instance, not only the effect of curing dermatitis of the manufactured skin care cream is reduced but also the period for which the cream product remains effective is remarkably curtailed.

If, on the other hand, shells are baked at temperature higher than 1,300° C., the effect of the manufactured skin care cream is not improved. Therefore, it is not desirable to bake shells at such a high temperature because it is only waste of energy.

While baked shell powder may be baked dead shell powder formed by baking/powdering or baked pearl shell powder formed by baking/powdering, the use of a combination of powder of baked pearl oyster shells and powder of baked pearls is desirable according to the results of the experiments conducted by the inventor of the present invention.

A method of manufacturing a skin care cream containing baked shell powder according to the present invention preferably includes: a first step of baking highly calcium-containing shells such as dead shells or pearls, crushing them to fine powder to obtain baked shell powder; a second step of mixing the obtained baked powder with water, agitating the mixture, leaving the mixture still to obtain supernatant water; a third step of adding the supernatant water obtained in the second step to the baked shell powder obtained in the first step and kneading the addition mixture; and a fourth step of further adding the dough obtained in the third step to and mixing it with a raw material for manufacturing cosmetic cream.

The baked shell powder is preferably powder of finely crushed shells with a particle size not more than 20 μm, preferably between 1 and 10 μm.

Any ordinary raw material for manufacturing cosmetic cream may be used for the purpose of the present invention. Examples of such raw materials include white petrolatum, stearyl alcohol, propylene glycol, polyoxyethylene hydrogenated castor oil, glyceryl monostearate and purified water.

More specific examples of such raw materials include behenyl alcohol, carnauba wax, stearic acid, white bees wax, petrolatum, paraffin, liquid paraffin, squalan, self-emulsifying glyceryl monostearate, phenoxyethanol, 1,3-butylene glycol, sorbit solution, 2-amino-2-methyl-propanol, vitamin A oil, natural vitamin E, pyridoxine dipalmitate, ascorbyl dipalmitate and purified water.

For a method of manufacturing a skin care cream containing baked shell powder according to the present invention, it is preferable to manufacture by adding both baked shell powder and unbaked shell powder to the raw material for manufacturing cosmetic cream and mixing them.

The effect of baked shell powder and that of pearl powder to the skin are coordinated when unbaked pearl powder is added.

EXAMPLES

Example 1

Firstly, the skin care cream containing baked shell powder and the method of manufacturing the same that utilized shell powder in Example 1 will be described below.

To obtain baked shell powder, dead shells of scallops, oysters, pearl oysters, abalones or pearls are baked at high temperature of 1,100° C. in a baking furnace for an hour and subsequently crushed to fine powder. Alternatively, dead shells may be crushed to fine powder first and then baked.

The obtained baked shell powder contains minerals including calcium that takes about 98% as well as magnesium, potassium, sodium, phosphorus, sulfur, zinc and so on for the balance.

As dead shells are baked at high temperature, they are mostly turned to quicklime (CaO), which is readily dissolved into water when brought into contact with the latter.

The maximum content ratio of such baked shell powder dissolved in water is 0.18%. In other words, strong alkaline water with about pH 12 is obtained simply by putting 2 g of baked shell powder into 1 liter of water.

In this example, pearl oyster shells were used to obtain baked shell powder, which was then added to and mixed with a raw material for manufacturing cosmetic cream to produce a cream containing baked shell powder. This will be described below.

Firstly, 10 g of the baked powder of pearl oyster shells obtained in the above-described manner was mixed with 1,000 cc of pure water, which was then stirred and subsequently left sill. After the elapse of a predetermined period of time, the supernatant water of the stirred water was filtered by means of a paper filter to obtain strong alkaline water containing fine baked powder.

150 cc of the strong alkaline water was then added to 1,000 g of a oil-in-water type base material prepared by putting 21 g of white petrolatum, 17 g of stearyl alcohol, 10 g of propylene glycol, 3.4 g of polyoxyethylene hydrogenated castor oil and 0.8 g of glyceryl monostearate into purified water and subsequently 5.75 g of baked powder of pearl oyster shell obtained by sorting out only 10 micron category particles was added to the base material to make it take 0.5% of the total weight. Then, the mixture was kneaded in a kneader to obtain a skin care cream containing shell powder that contained baked powder of pearl oyster shells by 0.62 g. Note that the oil-in-water type base material corresponds to a raw material for manufacturing cosmetic cream for the purpose of the present invention.

The prepared skin care cream containing baked shell powder was tested to find that it provided the following advantages when compared with conventional skin care creams prepared by using unbaked shell powder.

Conventional skin care creams prepared by using unbaked shell powder are mostly chemically neutral and their effects of curing athlete's foot and miliaria and anti-bacterial effects are very weak. To the contrary, the skin care cream prepared by adding baked shell powder obtained by baking shells at 1,100° C. was strongly alkaline and provided remarkably enhanced effects of curing athlete's foot and miliaria and anti-bacterial effects.

It is important not to simply bake dead shells but to bake them at high temperature higher than about 1,000° C. The above effects are weak if baked shell powder obtained by baking dead shells at temperature lower than the above cited level, for example at about 600° C., is used and the effects, if any, falls in a very short period of time (several days). To the contrary, it was found the skin care cream of this example maintained its strong effects for more than several years.

Dead shells for producing baked shell powder are not limited to those of pearl oysters and similar effects can be obtained by using shells of scallops, oysters, abalones or pearl oysters.

Example 2

While dead shells of pearl oysters were baked and a skin care cream was prepared by mixing baked shell powder of pearl oysters in Example 1, pearls were used in Example 2.

To obtain baked pearl powder, pearls taken out from shells of pearl oysters or pearl shells are baked at high temperature of 1,100° C. for an hour and subsequently crushed to fine powder.

The obtained baked pearl powder contains minerals including calcium that takes about 98% as well as magnesium, potassium, sodium, phosphorus, sulfur, zinc and so on for the balance.

As pearls are baked at high temperature, they are mostly turned to water-soluble calcium. The maximum content ratio of such baked pearl powder dissolved in water is 0.18%. In other words, strong alkaline water with about pH 12 is obtained simply by putting 2 g of baked pearl powder into 1 liter of water.

Then, 20 g of the baked pearl powder was mixed with 1,000 cc of mineral water containing no chlorine at all, which was then stirred and subsequently left sill. After the elapse of a predetermined period of time, the supernatant water of the stirred water was filtered by means of a paper filter to obtain strong alkaline water containing only fine baked pearl powder.

50 g of 1% solution of sodium hyaluronate, 6.5 g of baked pearl powder, 1.5 g of 10 micron category unbaked pearl powder, 10 g of glycerin and 7 g of ethanol were put into 200 g of the strong alkaline water and the mixture was kneaded.

The obtained mineral cream base material was kneaded with petrolatum, stearyl alcohol, PEG-60 hydrogenated castor oil, glyceryl stearate and propylene glycol in a kneader for about two hours to obtain a uniform mixture. Note that the kneaded mixture corresponds to a raw material for manufacturing cosmetic cream for the purpose of the present invention.

The skin care cream obtained as a result of the kneading contained 19.57 g of petrolatum, 15.66 g of stearyl alcohol, 9.33 g of propylene glycol, 3.13 g of PEG-60 hydrogenated castor oil, 3.92 g of sodium hyaluronate, 0.78 g of glycerin, 0.78 g of glyceryl stearate, 0.62 g of baked pearl powder, 0.55 g of ethanol, 0.11 g of pearl powder and an appropriate amount of water.

The skin care cream containing backed pearl powder was tested to find that it provided the following advantages when compared with conventional skin care creams prepared by using unbaked shell powder. Conventional skin care creams prepared by using unbaked shell powder are mostly chemically neutral and their effects of curing athlete's foot and miliaria and anti-bacterial effects are very weak. To the contrary, the skin care cream prepared by adding baked pearl powder obtained by baking pearls at 1,100° C. was strongly alkaline and provided remarkably enhanced effects of curing athlete's foot and miliaria and anti-bacterial effects.

Table 1 below shows the compositions of the skin care creams containing baked shell powder of Examples 1 and 2.

TABLE 1

| per 100 g of cream | | |
|---|---|---|
| | Example 1 | Example 2 |
| white petrolatum | 21 g | 19.57 g |
| stearyl alcohol | 17 g | 15.66 g |
| propylene glycol | 10 g | 9.39 g |
| polyoxyethylene hydrogenated castor oil 60 | 3.4 g | 3.13 g |
| glyceryl monostearate | 0.8 g | |
| baked pearl oyster shell powder | 0.62 g | |
| glyceryl stearate | | 0.70 g |
| ethanol | | 0.55 g |
| pearl powder (unbaked) | | 0.11 g |
| baked pearl powder | | 0.62 g |
| sodium hyaluronate | | 3.90 g |
| glycerin | | 0.78 g |
| pure water | 47.02 g | 45.48 g |

FIG. 1 illustrates the effects of the skin care creams containing baked shell powder.

Alternatively, the pearl layer formed on the inner surface of each dead shell of pearl oyster or each pearl shell may be separated from the shell, baked like the shells and the pearls in Examples 1 and 2 and kneaded to produce a cream. A product that is as effective as or more effective than the products of Examples 1 and 2 can be obtained by way of this alternative process.

What is claimed is:

1. A method of manufacturing a skin care cream, comprising:
   a first step of
      baking highly calcium-containing shells including dead shells and/or pearls at 1,000-1,300° C., and
      crushing the calcium-containing shells to fine powder to obtain baked shell powder and/or baked pearl powder;
   a second step of
      mixing the portioned baked shell powder and/or baked pearl powder with water to obtain a mixture,
      agitating the mixture,
      leaving the mixture still to obtain a supernatant water, and separating the supernatant water from the mixture and filtering the supernatant water to obtain a strong alkaline water;

a third step of adding the strong alkaline water obtained in the second step to another portion of the baked shell powder and/or baked pearl powder obtained in the first step to obtain an addition mixture, and kneading the addition mixture to obtain a dough; and a fourth step of further adding the dough obtained in the third step to and mixing the dough with a raw material of a cosmetic cream thereby manufacturing a skin care cream.

2. The method of manufacturing a skin care cream according to claim 1, wherein the baked shell powder and/or baked pearl powder is formed by baking and powdering the dead shells and/or the pearl.

3. The method of manufacturing a skin care cream according to claim 1, wherein unbaked shell powder and/or unbaked pearl powder is further added to and mixed with the raw material of the cosmetic cream thereby manufacturing the skin care cream.

4. The method of manufacturing a skin care cream according to claim 3, wherein the baked pearl powder and the unbaked pearl powder are added to and mixed with the raw material of the cosmetic cream thereby manufacturing the skin care cream.

5. The method of manufacturing a skin care cream according to claim 1, wherein the dead shells are shells selected from the group consisting of scallops, oysters, pearl oysters, and abalones.

6. The method of manufacturing a skin care cream according to claim 1, wherein calcium-containing shells are a mixture of the dead shells and the pearls.

7. The method of manufacturing a skin care cream according to claim 1, wherein calcium-containing shells are the dead shells.

8. The method of manufacturing a skin care cream according to claim 1, wherein calcium-containing shells are the pearls.

9. The method of manufacturing a skin care cream according to claim 1, wherein a pH of the strong alkaline water is at least 12.

* * * * *

UNITED STATES PATENT AND TRADEMARK OFFICE
CERTIFICATE OF CORRECTION

| | |
|---|---|
| PATENT NO. | : 8,323,699 B2 |
| APPLICATION NO. | : 12/656077 |
| DATED | : December 4, 2012 |
| INVENTOR(S) | : Kaunobu Sanada |

It is certified that error appears in the above-identified patent and that said Letters Patent is hereby corrected as shown below:

Please add the information to Related U.S. Application Data on Title Page item [62];

--Division of application No. 11/884,023, filed on Aug. 9, 2007, now abandoned, which is PCT National Phase of International application number PCT/JP2006/302391 filed on 02/10/2006.--.

Signed and Sealed this
Twenty-second Day of January, 2013

David J. Kappos
*Director of the United States Patent and Trademark Office*